(12) United States Patent
Ajima

(10) Patent No.: US 11,350,856 B2
(45) Date of Patent: Jun. 7, 2022

(54) ELECTRONIC DEVICE AND ESTIMATION SYSTEM

(71) Applicant: KYOCERA Corporation, Kyoto (JP)

(72) Inventor: Hiromi Ajima, Kawasaki (JP)

(73) Assignee: KYOCERA Corporation, Kyoto (JP)

( * ) Notice: Subject to any disclaimer, the term of this patent is extended or adjusted under 35 U.S.C. 154(b) by 372 days.

(21) Appl. No.: 16/086,329

(22) PCT Filed: Mar. 24, 2017

(86) PCT No.: PCT/JP2017/012083
§ 371 (c)(1),
(2) Date: Sep. 19, 2018

(87) PCT Pub. No.: WO2017/175608
PCT Pub. Date: Oct. 12, 2017

(65) Prior Publication Data
US 2019/0090793 A1    Mar. 28, 2019

(30) Foreign Application Priority Data

Apr. 8, 2016 (JP) .............................. JP2016-077938

(51) Int. Cl.
*A61B 5/145* (2006.01)
*A61B 5/02* (2006.01)
*A61B 5/1455* (2006.01)
*A61B 5/00* (2006.01)
(Continued)

(52) U.S. Cl.
CPC ............ *A61B 5/14532* (2013.01); *A61B 5/02* (2013.01); *A61B 5/1455* (2013.01); *A61B 5/6824* (2013.01); *A61B 5/0059* (2013.01); *A61B 5/681* (2013.01); *A61B 2562/0233* (2013.01)

(58) Field of Classification Search
CPC ..... A61B 5/14532; A61B 5/02; A61B 5/6824; A61B 5/1455; A61B 5/0059; A61B 5/681; A61B 2562/0233; A61B 5/02116; A61B 5/02028; A61B 5/6822; A61B 5/7239; A61B 5/7246; A61B 5/7257;
(Continued)

(56) References Cited

U.S. PATENT DOCUMENTS

| 9,603,521 B2 | 3/2017 | Cho et al. |
| 10,085,656 B2 | 10/2018 | Sato |
| 2002/0188210 A1 | 12/2002 | Aizawa |

(Continued)

FOREIGN PATENT DOCUMENTS

| JP | 2002-360530 A | 12/2002 |
| JP | 2010-510010 A | 4/2010 |

(Continued)

OTHER PUBLICATIONS

Machine Translation of RU 2473307C1 (Year: 2013).*

*Primary Examiner* — Devin B Henson
*Assistant Examiner* — Justin Xu
(74) *Attorney, Agent, or Firm* — Studebaker & Brackett PC

(57) ABSTRACT

This electronic device includes a sensor that acquires a pulse wave of a subject, and a controller that estimates the blood glucose level of the subject on the basis of an estimation expression that is created on the basis of a blood glucose level and a pulse wave corresponding to the blood glucose level, and the pulse wave of the subject acquired by the sensor.

12 Claims, 16 Drawing Sheets

(51) Int. Cl.
*A61B 5/021* (2006.01)
*A61B 5/024* (2006.01)

(58) Field of Classification Search
CPC . A61B 5/02444; A61B 5/14546; A61B 5/024; A61B 5/02438
See application file for complete search history.

(56) References Cited

U.S. PATENT DOCUMENTS

| | | | |
|---|---|---|---|
| 2003/0208113 A1* | 11/2003 | Mault | A61B 5/14532 600/316 |
| 2004/0106872 A1* | 6/2004 | Kosuda | A61B 5/02438 600/485 |
| 2010/0056880 A1 | 3/2010 | Cho et al. | |
| 2012/0059237 A1* | 3/2012 | Amir | A61B 5/0285 600/365 |
| 2017/0209055 A1* | 7/2017 | Pantelopoulos | A61B 5/02108 |
| 2018/0008175 A1 | 1/2018 | Ishizawa et al. | |

FOREIGN PATENT DOCUMENTS

| | | |
|---|---|---|
| JP | 2012-019834 A | 2/2012 |
| JP | 2013-121420 A | 6/2013 |
| RU | 2473307 C1 * | 1/2013 |
| WO | 2010/128500 A2 | 11/2010 |
| WO | 2016/147795 A1 | 9/2016 |

\* cited by examiner

ELECTRONIC DEVICE AND ESTIMATION SYSTEM

REFERENCE TO CORRESPONDING APPLICATION

This application claims the priority of Japanese Patent Application No. 2016-077938 (filed on 8 Apr. 2016), the entire disclosure of which is hereby incorporated herein by reference.

TECHNICAL FIELD

The present disclosure relates to an electronic device and to an estimation system that estimate the state of health of a subject from measured biological information.

BACKGROUND

In the prior art, as a means for estimating the state of health of a subject (i.e. a user), measurement of blood components and measurement of blood fluidity have been performed. These measurements are performed by using blood that has been sampled from the subject. Moreover, electronic devices that measure biological information from test sites such as the wrist of the subject and so on are known. For example, a known electronic device is fitted upon the wrist of the subject and measures the pulse of the subject.

SUMMARY

An electronic device according to an embodiment comprises: a sensor that acquires a pulse wave of a subject, and a controller that estimates the blood glucose level of the subject on the basis of an estimation expression created on the basis of a blood glucose level and a pulse wave corresponding to the blood glucose level, and the pulse wave of the subject acquired by the sensor.

And an electronic device according to an embodiment comprises: a sensor that acquires a pulse wave of a subject, and a controller that estimates a lipid value of the subject on the basis of an estimation expression created on the basis of a blood glucose level and a pulse wave corresponding to the blood glucose level, and the pulse wave of the subject acquired by the sensor.

An estimation system according to an embodiment comprises a blood glucose meter that measures a blood glucose level of a subject, and an electronic device having a sensor that acquires a pulse wave of the subject, wherein the electronic device estimates the blood glucose level of the subject on the basis of an estimation expression created on the basis of a blood glucose level and a pulse wave corresponding to the blood glucose level, the blood glucose level of the subject measured by the blood glucose meter, and the pulse wave of the subject acquired by the sensor.

An estimation system according to an embodiment comprises a blood glucose meter that measures a blood glucose level of a subject, and an electronic device having a sensor that acquires a pulse wave of the subject, wherein the electronic device estimates a lipid value of the subject on the basis of an estimation expression created on the basis of a blood glucose level and a pulse wave corresponding to the blood glucose level, the blood glucose level of the subject measured by the blood glucose meter, and the pulse wave of the subject acquired by the sensor.

DETAILED DESCRIPTION

In cases where a blood component or the blood fluidity of a subject is measured by using blood sampled from the subject, it is difficult to estimate the state of health of the subject on a daily basis because it is necessary to perform blood sampling, which is accompanied by pain. According to the present disclosure, it is possible to provide an electronic device and an estimation system that are capable of estimating the state of health of a subject in a convenient manner.

Embodiments will now be explained with reference to the drawings.

Embodiment 1

Figure 1:
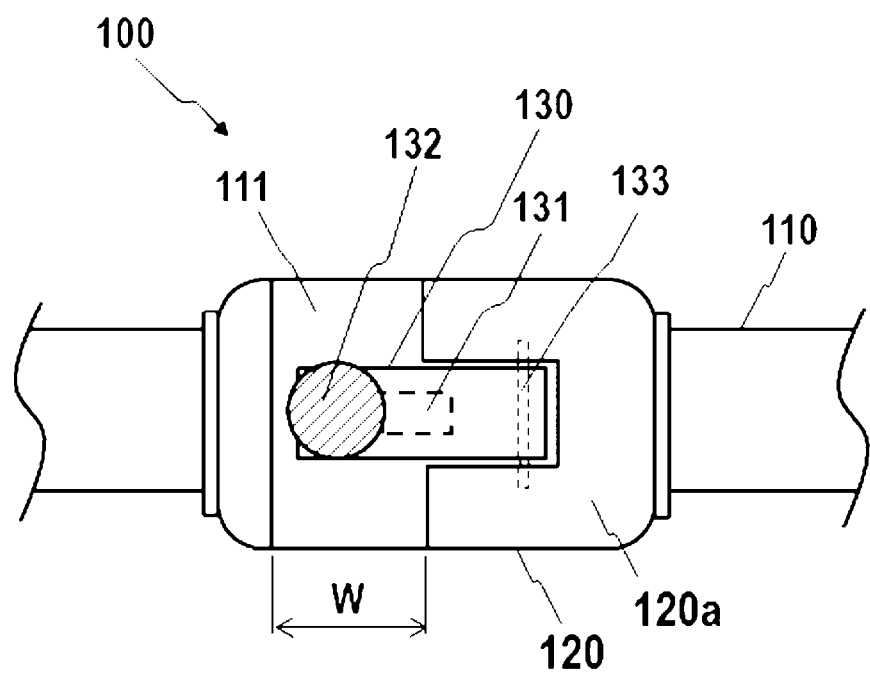
FIG. 1 is a schematic diagram illustrating the general structure of an electronic device according to a first embodiment.

FIG. 1 is a schematic diagram illustrating the general structure of an electronic device according to a first embodiment. The electronic device 100 comprises a wearing portion 110 and a measurement unit 120. FIG. 1 is a diagram in which the electronic device 100 is viewed looking at its rear surface 120a, which is contacted against a portion of the subject to be examined.

In the state in which the electronic device 100 is worn by the subject, the electronic device 100 measures biological information of the subject. The biological information measured by the electronic device 100 is a pulse wave of the subject that can be measured by the measurement unit 120. In the following explanation of this embodiment it will be assumed, as one example, that the electronic device 100 is worn on the wrist of the subject and acquires the pulse wave.

In this embodiment, the wearing portion 110 is a long and narrow band formed in a linear shape. The measurement of the pulse wave may be performed, for example, in the state in which the subject has wrapped the wearing portion 110 of the electronic device 100 around his wrist. In concrete terms, the subject performs measurement of his pulse wave by wrapping the wearing portion 110 around his wrist so that the rear surface 120a of the measurement unit 120 is in contact with the test site. The electronic device 100 measures the pulse wave of the blood flowing in the ulnar artery or in the radial artery on the wrist of the subject.

Figure 2:
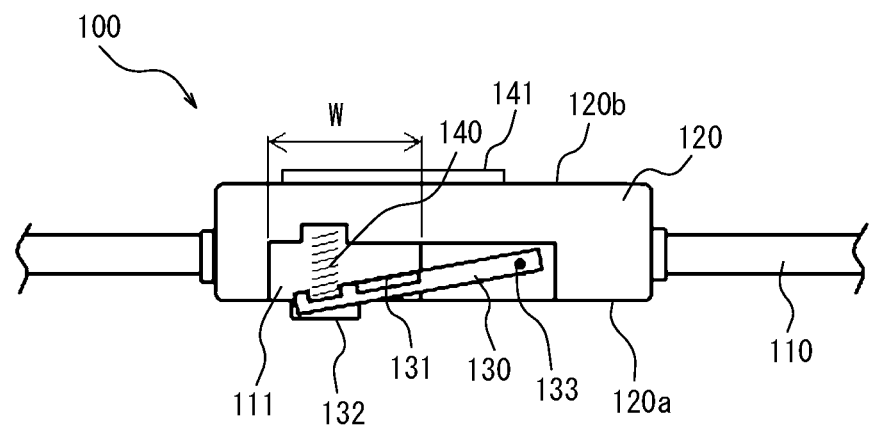
FIG. 2 is a sectional view illustrating the general structure of a main body portion of FIG. 1.

FIG. 2 is a sectional view illustrating the general structure of the measurement unit 120 of FIG. 1. Along with the measurement unit 120, parts of the wearing portion 110 near the measurement unit 120 are also illustrated in FIG. 2.

The measurement unit 120 has a rear surface 120a that contacts against the wrist of the subject when worn, and a front surface 120b on its side opposite from the rear surface 120. The measurement unit 120 also has an opening 111 on its rear surface 120a. A sensor 130 is supported by the measurement unit 120, and, in a state in which an elastic member 140 is not being pressed, one end of the sensor protrudes from the rear surface 120a at the opening 111. The one end of the sensor 130 is provided with a pulse application portion 132. The one end of the sensor 130 can be displaced in a direction almost perpendicular to the rear surface 120a. The other end of the sensor 130 is supported by the measurement unit 120 via a support 133, so that the one end of the sensor 130 can be displaced in this way.

The one end of the sensor 130 is in contact with the measurement unit 120 via the elastic member 140 and is displaceable. The elastic member 140 may, for example, be a spring. However the elastic member 140 is not limited to being a spring; any other suitable elastic member may be used, such as, for example, one made from resin or sponge material or the like.

Although not illustrated, a controller, a memory, a communication interface, a power source, a notification interface, circuitry for enabling those to operate, connection cables and so on may be provided to the measurement unit 120.

The sensor 130 includes an angular velocity sensor 131 that detects displacement of the sensor 130. This angular velocity sensor 131 should be able to detect angular displacement of the sensor 130. The sensor provided to the sensor 130 is not limited to being such an angular velocity sensor 131; it will be acceptable for it to be, for example, an acceleration sensor, an angle sensor, or some other type of motion sensor, and the sensor may also include a plurality of such sensors.

The electronic device 100 also comprises an input interface 141 on the front surface 120b of the measurement unit 120. This input interface 141 is a section that receives operational input from the subject, and may, for example, include operation buttons (i.e. operation keys). Or, for example, the input interface 141 could also include a touch screen.

Figure 3:
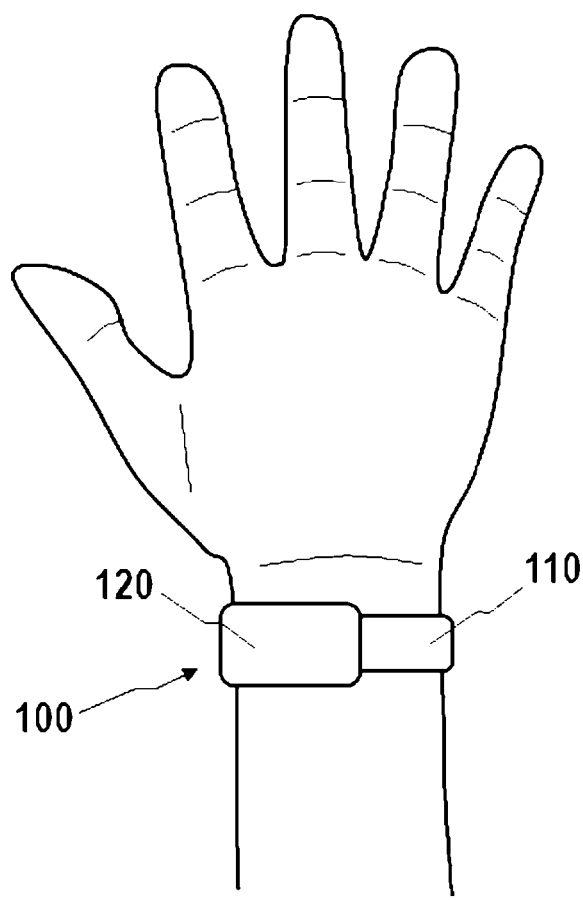
FIG. 3 is a diagram illustrating an example of the way in which the electronic device of FIG. 1 is used.

FIG. 3 is a diagram illustrating an example of the way in which the electronic device 100 is used by a subject. The subject uses the electronic device 100 by wrapping it around his wrist. The electronic device 100 is mounted in a state in which the rear surface 120a of the measurement unit 120 is in contact with the test portion of the subject's wrist. In the state in which the wearing portion 110 wrapped around the subject's wrist, the position of the measurement unit 120 can be adjusted so that the pulse application portion 132 contacts against the portion where the ulnar artery or the radial artery is present.

In FIG. 3, in the state in which the electronic device 100 is worn, one end of the sensor 130 is in contact with the skin of the subject above the radial artery, which is the artery on the thumb side of the left hand. The one end of the sensor 130 is held in contact against the skin above the radial artery of the subject, due to the elastic force of the elastic member 140 that is disposed between the measurement unit 120 and the sensor 130. Thus, the sensor 130 is displaced in accordance with movement of the radial artery of the subject, in other words in accordance with its pulsations. The angular velocity sensor 131 acquires the pulse waves by detecting displacement of the sensor 130. A waveform that captures, from the surface of the body of the subject, the change over time of the volume of a blood vessel caused by inflow of blood is termed a pulse wave.

Referring to FIG. 2, in the state in which the elastic member 140 is not being pressed, the sensor 130 is in a state in which one end thereof is protruding from the opening 111. When the electronic device 100 has been attached to the subject, this one end is contacted against the skin above the radial artery of the subject. According to the arterial pulsations, the elastic member 140 expands and contracts, and the one end of the sensor 130 is displaced. The material used for the elastic member 140 has a moderate modulus of elasticity, so that it does not oppose any substantial hindrance to the pulsations, and so that it can expand and contract according to the pulsations. The opening width W of the opening 111 is set to be somewhat larger than the diameter of the blood vessel. In this embodiment, the opening width W is somewhat larger than the diameter of the radial artery. Due to the provision of the opening in the measurement unit 120, in the state in which the electronic device 100 is worn by the subject, the rear surface 120a of the measurement unit 120 does not press upon his radial artery. For this reason, the electronic device 100 is capable of acquiring the pulse wave with little noise, and the accuracy of the measurement is enhanced.

In FIG. 3 an example is illustrated in which the electronic device 100 is fitted upon the wrist of the subject and acquires the pulse wave in the radial artery, but this is not to be considered as being limitative of the present disclosure. For example, it would also be acceptable to arrange for the electronic device 100 to acquire the pulse wave of blood flowing in the carotid artery in the neck of the subject. In concrete terms, the subject may lightly press the pulse application portion 32 against the position of his carotid artery, and thereby perform measurement of the pulse wave thereof. The subject may wrap the wearing portion 110 around the neck, so that the pulse application portion 132 becomes positioned over the carotid artery.

Figure 4:
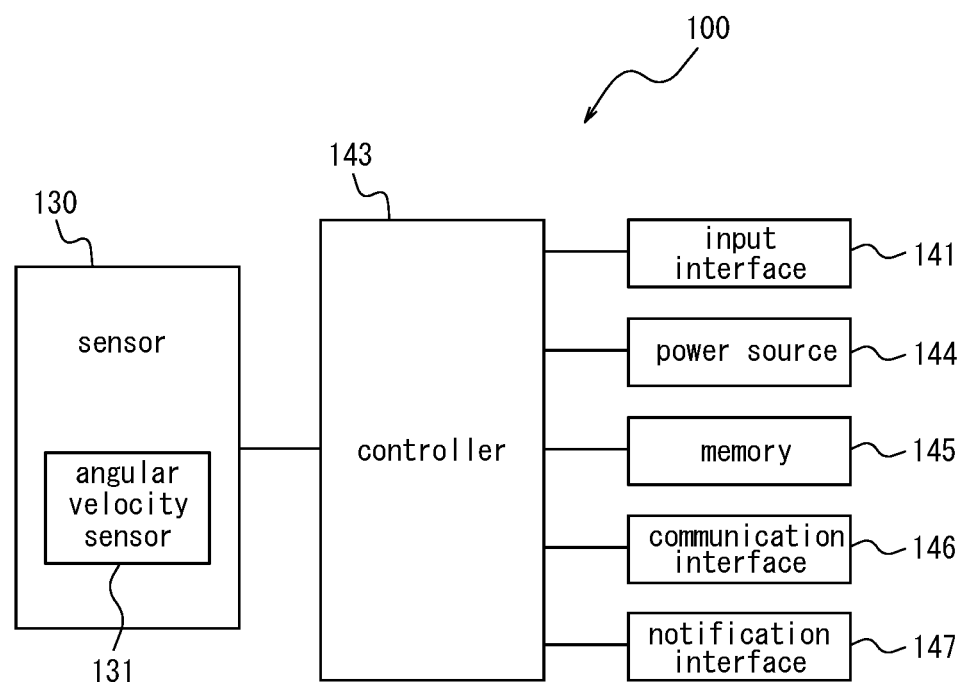
FIG. 4 is a functional block diagram illustrating the general structure of the electronic device of FIG. 1.

FIG. 4 is a functional block diagram illustrating the general structure of the electronic device 100. The electronic device 100 comprises a sensor 130, an input interface 141, a controller 143, a power source 144, a memory 145, a communication interface 146, and a notification interface 147. In this embodiment, the controller 143, the power source 144, the memory 145, the communication interface 146, and the notification interface 147 are included in the interior of the measurement unit 120 or the wearing portion 110.

The sensor 130 includes the angular velocity sensor 131, and acquires a pulse wave by detecting pulsations at the test site.

The controller 143 is a processor that controls and manages the electronic device 100 as a whole, including each of the functional blocks of the electronic device 100. The controller 143 is a processor that estimates the blood glucose level of the subject from the pulse wave that has been acquired. The controller 143 includes a processor such as a CPU (Central Processing Unit) and so on, and executes a program specifying the details of a control procedure and a program that estimates the blood glucose level of the subject. These programs are stored upon a storage medium, such as for example the memory 145 or the like. On the basis of a calculated index, the controller 143 estimates a state related to the glucose metabolism or the lipid metabolism or the like of the subject. The controller 143 also issues data notifications to the notification interface 147.

The power source 144 may comprise, for example, a lithium ion battery and control circuitry for charging and discharging thereof and so on, and supplies electrical power to the entire electronic device 100.

The memory 145 stores programs and data. The memory 145 may include a non-volatile storage medium of any suitable type, such as a semiconductor storage medium or a magnetic storage medium or the like. And the memory 145 may include storage mediums of a plurality of types. The memory 145 may include a combination of a portable storage medium such as a memory card, an optical disk, an opto-magnetic disk or the like, and a reading device for that storage medium. Moreover, the memory 145 may include a storage device that is employed as a temporary storage area, such as RAM (Random Access Memory) or the like. The memory 145 stores information of various types and programs for causing the electronic device 100 to operate and so on, and also functions as a working memory. The memory 145 may, for example, store the results of pulse wave measurement acquired by the sensor 130.

The communication interface 146 exchanges data of various types with an external device by performing wired communication or wireless communication. For example, the communication interface 146 may perform communication with an external device that stores bio-information about the subject in order to manage a health state, and may transmit the results of measurement of the subject's pulse wave by the electronic device 100 and the health state as estimated by the electronic device 100 to that external device.

The notification interface 147 notifies information via sound, vibration, images, or the like. The notification interface 147 may comprise a display device such as a speaker, a vibrator, a liquid crystal display (LCD: Liquid Crystal Display), an organic EL display (OELD: Organic Electro-Luminescence Display), or an inorganic EL display (IELD: Inorganic Electro-Luminescence Display) or the like. In this embodiment, the notification interface 147 may notify, for example, the state of the glucose metabolism or the lipid metabolism of the subject.

The electronic device 100 estimates the blood glucose level of the subject on the basis of an estimation expression that has been created by regression analysis. The electronic device 100 may, for example, store this estimation expression for estimating the blood glucose level on the basis of the pulse wave in the memory 145 in advance. The electronic device 100 estimates the blood glucose level by employing this estimation expression.

Now, the theory related to estimation of blood glucose level on the basis of the pulse wave will be explained. After eating, due to elevation of the blood glucose level in the blood, a decrease in the blood fluidity (i.e. an increase in its viscosity), dilation of the blood vessels, and an increase in the circulating blood volume take place, and the state of motion of the blood vessels and the state of motion of the blood are determined so that these states are in equilibrium. Decrease of the fluidity of the blood may occur, for example, as a result of increase in the viscosity of the blood plasma and reduction of the deformability of the red blood cells. Expansion of the blood vessels may occur as a result of the secretion of insulin, the secretion of digestive hormones, a rise in body temperature, and so on. As the blood vessels expand, the pulse rate increases in order to prevent reduction of the blood pressure. An increase in the circulating blood volume also supplements consumption of blood due to digestion and absorption. Because of these causes, changes of the state of motion of the blood vessels and change of the state of motion of the blood between before eating and after eating are also reflected in the pulse wave. Due to this, the electronic device 100 acquires the pulse waves, and is able to estimate the blood glucose level on the basis of changes in the waveforms of the pulse waves that have been acquired.

On the basis of the estimation theory described above, the estimation expression for estimation of the blood glucose level can be created by performing regression analysis on the basis of sample data obtained from a plurality of test subjects for blood glucose levels and pulse waves before eating and after eating. At the time of estimation, the blood glucose level of the subject can be estimated by applying this estimation expression that has thus been created to an index based upon the pulse wave of the subject. In creation of the estimation expression, it is possible to estimate the blood glucose level of the subject who will be the test subject by performing regression analysis and creating an estimation expression using sample data in which the variation of blood glucose level is close to a normal distribution, irrespective of whether or not this is before eating or after eating.

Figure 5:
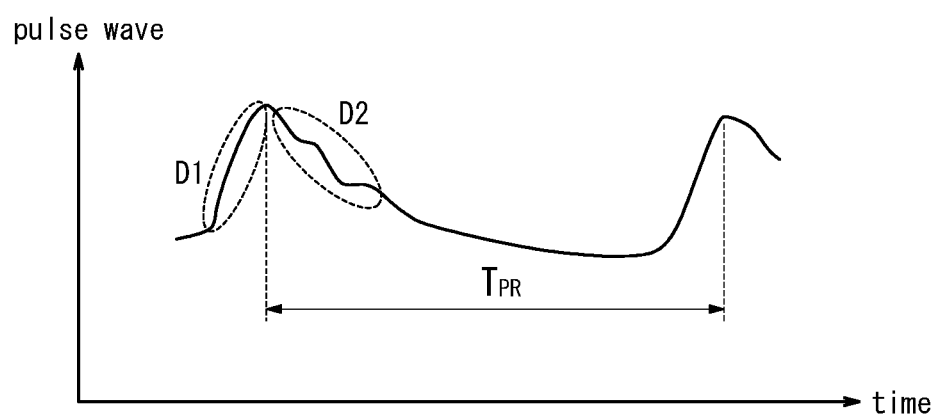
FIG. 5 is a diagram for explanation of an example of a method for estimation by the electronic device of FIG. 1 based upon change of a pulse wave.

FIG. 5 is a diagram for explanation of an example of an estimation method based upon change of pulse wave, and illustrates an example of a pulse wave. An estimation expression for estimating the blood glucose level may be created by performing regression analysis upon, for example, the index (the rising index) S1 that characterizes the rising slope of the wave, the AI (Augmentation Index), and the pulse rate PR.

Figure 6:
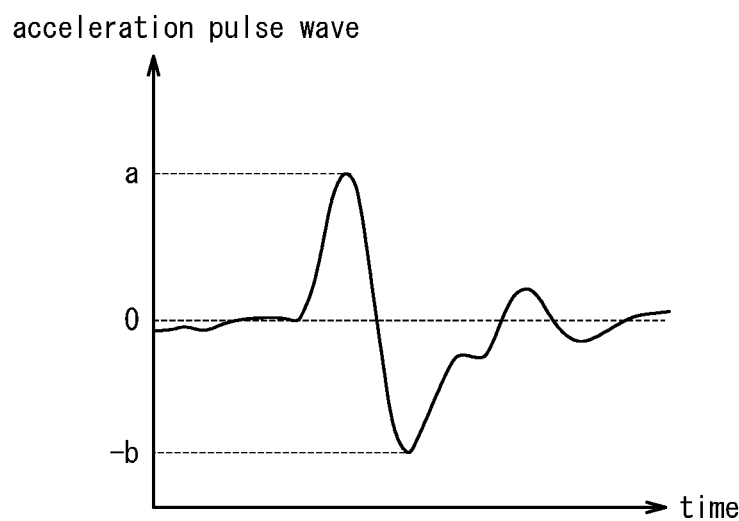
FIG. 6 is a diagram illustrating an example of an acceleration pulse wave.

The rising index S1 is derived on the basis of the waveform illustrated in the region D1 of FIG. 5. In concrete terms, the rising index S1 is the ratio of the first minimum value to the first maximum value in the acceleration pulse wave, which is derived by differentiating the pulse wave twice. As illustrated in FIG. 6 by way of example, the rising index S1 is given by −b/a in the acceleration pulse wave. The rising index S1 decreases due to reduction in the blood fluidity after eating, secretion of insulin, dilatation (i.e. relaxation) of the blood vessels due to a rise in body temperature, and so on.

Figure 7:
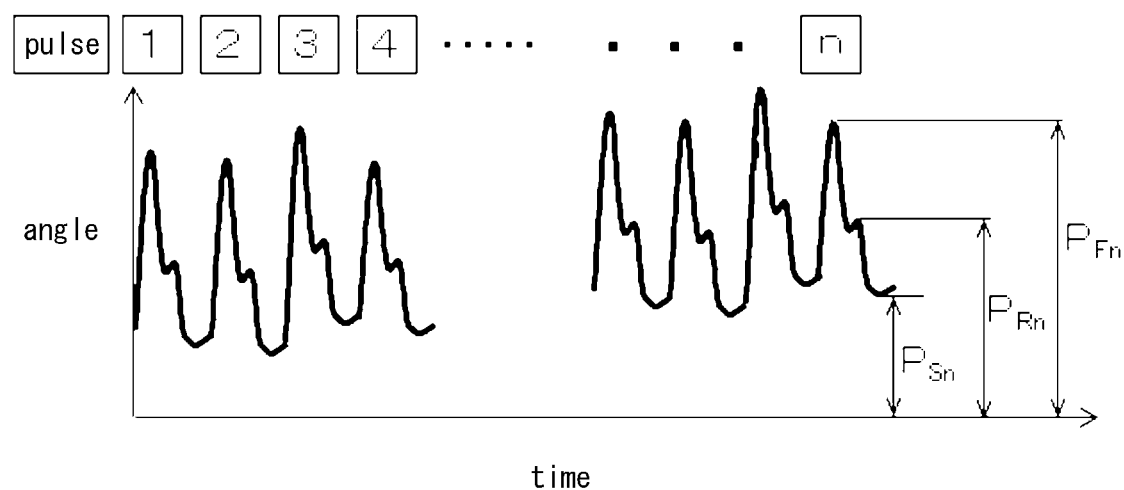
FIG. 7 is a diagram illustrating an example of a pulse wave acquired by a sensor.

The AI is an index that is given by the ratio of the magnitudes of the forward and the reflected waves of the pulse wave. A method for derivation of the AI will now be explained with reference to FIG. 7. FIG. 7 is a diagram illustrating an example of a pulse wave acquired by employing the electronic device 100 as fitted to the wrist of a subject. FIG. 7 illustrates a case in which an angular velocity sensor 131 is used as the pulsation detection means. FIG. 7 displays the time integral of the angular velocity acquired by the angular velocity sensor 131. In FIG. 7, time is shown along the horizontal axis and angle is shown along the vertical axis. Since in some cases the pulse wave that has been acquired may include noise caused, for example, by the subject moving his body, accordingly it would be possible to perform correction with a filter that eliminates the DC (Direct Current) component, so that only the pulsation component is extracted.

Pulse wave propagation is a phenomenon by which pulsations due to blood being expelled from the heart are transmitted through the walls of arteries or via the blood. Pulsations due to blood expelled from the heart reach the extremities of the limbs as forward waves, and parts of these forward waves are reflected by branching portions of the blood vessels and locations where the diameters of the blood vessels change and so on, and are returned as reflected waves. AI is the amplitude of these reflected waves divided by the amplitude of the forward waves, and is given by $AI_n = (P_{Rn} - P_{Sn})/(P_{Fn} - P_{Sn})$. Here, $AI_n$ is the AI for each pulse. It would also be acceptable, for example, for AI to be obtained by performing measurement of the pulse wave for several seconds, and then calculating the average value per pulse $AI_{ave}$ for each pulse $AI_n$ (where n is an integer from 1 to n). AI is derived on the basis of the waveform illustrated in the region D2 of FIG. 5. AI decreases after eating, because of a reduction in the fluidity of the blood and an expansion of the blood vessels due to a rise in body temperature and so on.

The pulse rate PR is derived on the basis of the period $T_{PR}$ of the pulse wave illustrated in FIG. 5. The pulse rate P rises after eating.

The electronic device 100 is able to estimate the blood glucose level according to an estimation expression that is created on the basis of these values, i.e. the rising index S1, AI, and the pulse rate PR.

Figure 8A:
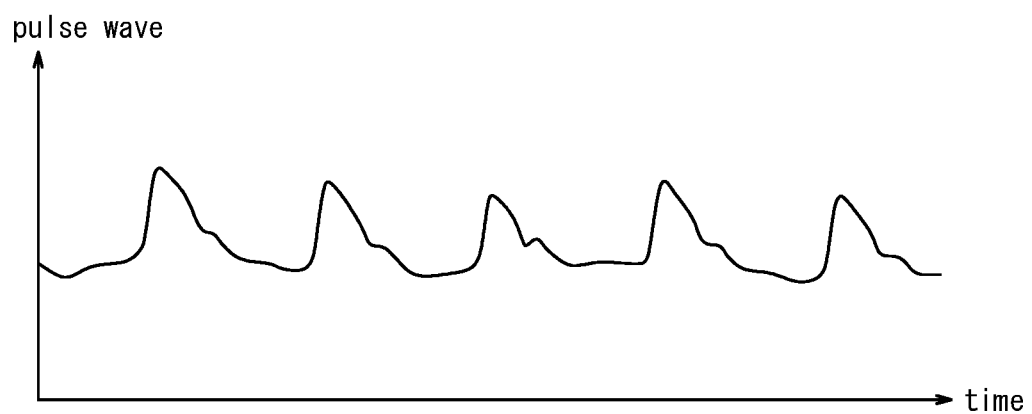
FIGS. 8A and 8B are diagrams for explanation of another example of a method for estimation by the electronic device of FIG. 1 based upon change of a pulse wave.
Figure 8B:
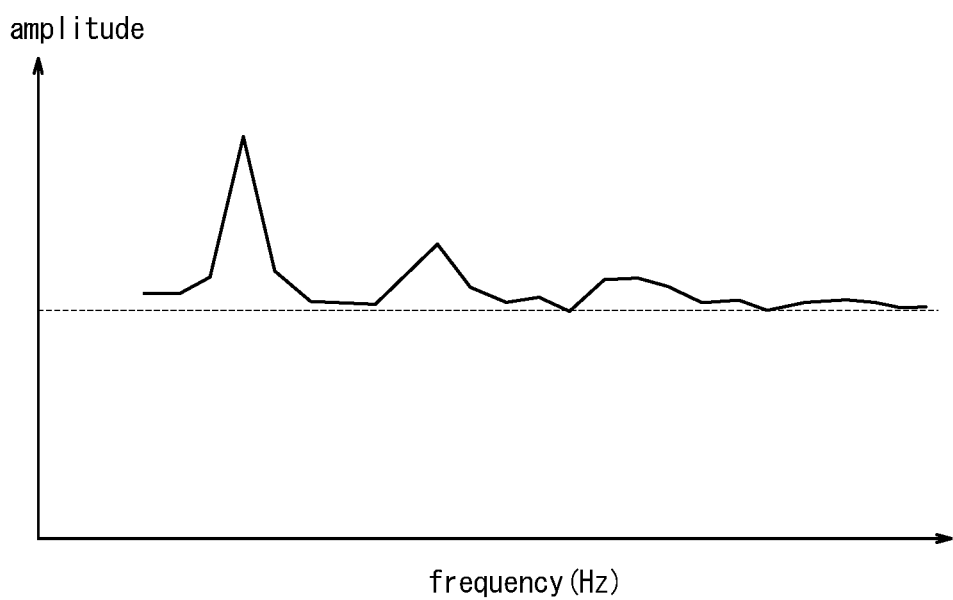

FIG. 8 is a diagram for explanation of another example of a method for estimation on the basis of change of the pulse wave. FIG. 8A illustrates the pulse wave, and FIG. 8B illustrates the result of performing an FFT (i.e. a fast Fourier transform: Fast Fourier Transform) upon the pulse wave illustrated in FIG. 8A. The estimation expression for estimation of the blood glucose level may, for example, be created by performing regression analysis related to the fundamental wave and the harmonic components (i.e. the Fourier coefficients) derived by the FFT. The peak value in the FFT results illustrated in FIG. 8B varies on the basis of change of the waveform of the pulse wave. Accordingly, it is possible to estimate the blood glucose level according to an estimation expression that is created on the basis of the Fourier coefficients.

The electronic device 100 estimates the blood glucose level of the subject by using the estimation expression based upon the rising index S1, upon the AI, upon the pulse rate PR, and upon the Fourier coefficients and so on described above.

Now, a method for creating the estimation expression that the electronic device 100 employs when estimating the blood glucose level of the subject will be explained. There is no need for creation of this estimation expression to be performed by the electronic device 100. The estimation expression may alternatively be created in advance by using a different computer or the like. In this specification, the explanation will refer to the device that creates the estimation expression as the "estimation expression creation device". After having been created, the estimation expression is stored in the memory 145, for example before estimation of blood glucose level is performed by the electronic device 100.

Figure 9:
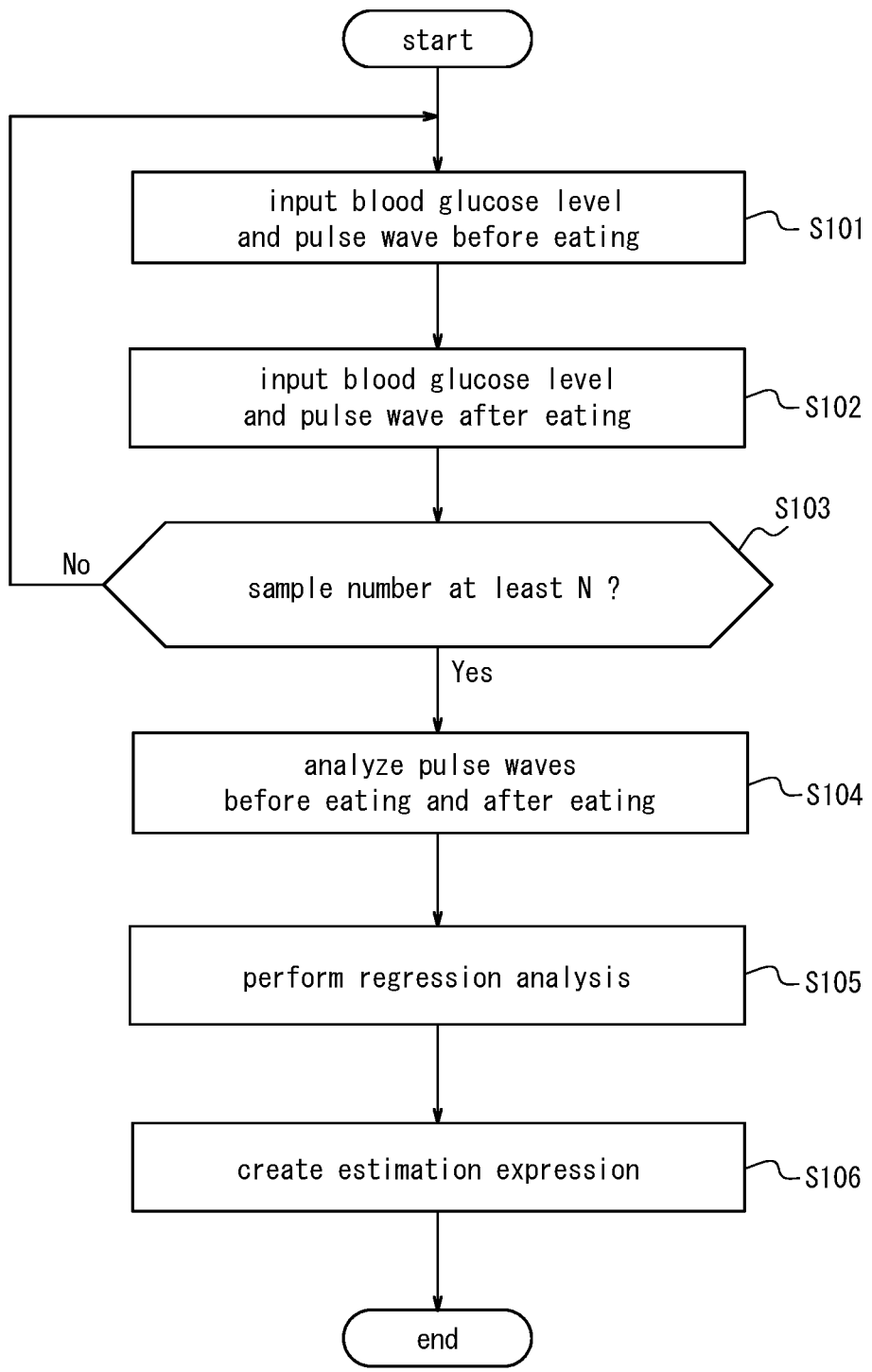
FIG. 9 is a flow chart illustrating creation of an estimation expression used by the electronic device of FIG. 1.

FIG. 9 is a flow chart illustrating a flow for creation of an estimation expression used by the electronic device 100 of FIG. 1. The pulse waves of a subject are measured before eating and after eating by employing a pulse wave meter, the blood glucose levels of the subject before eating and after eating are also measured by employing a blood glucose meter, and the estimation expression is created by performing regression analysis on the basis of the sample data obtained by those measurements. It should be understood that "before eating" means when the stomach of the subject is empty, while "after eating" means after a certain time period has elapsed after eating for the blood glucose level to rise (for example, about one hour after the subject has started eating). The sample data that may be acquired is not limited to being before eating and after eating, provided that it is data in a time band in which the fluctuations of blood glucose level are large.

For creation of the estimation expression, first, information related to the blood glucose level of the subject before eating and to the pulse wave associated with this blood glucose level, as measured by a blood glucose meter and by a pulse wave meter respectively, is inputted to the estimation expression creation device (step S101).

The information related to the blood glucose level of the subject after eating and to the pulse wave associated with this blood glucose level as measured by the blood glucose meter and by the pulse wave meter respectively is inputted to the estimation expression creation device (step S102). The blood glucose levels inputted in steps S101 and S102 may, for example, be measured by the blood glucose meter by performing blood sampling. For each of the sets of sample data, the age of the subject is also inputted in step S101 or step S102.

The estimation expression creation device then determines whether the number of samples in the sample data inputted in step S101 and step S102 is at least a number N that is sufficient for performing regression analysis (step S103). The number of samples N may be determined in any appropriate manner; for example, it may be set to 100. If the estimation expression creation device determines that the number of samples is less than N (the No case), then step S101 and step S102 are repeated until the number of samples N becomes N or greater. On the other hand, if the estimation expression creation device determines that the number of samples is at least N (the Yes case), then the flow of control proceeds to step S104, and calculation of the estimation expression is performed.

In this calculation of the estimation expression, the estimation expression creation device analyzes the pulse waves before eating and after eating (step S104). In this embodiment, the estimation expression creation device performs analysis of the rising indexes S1, of the AI, and of the pulse rates PR before eating and after eating. The estimation expression creation device may perform FFT analysis as analysis of the pulse waves.

The estimation expression creation device then performs regression analysis (step S105). The objective variable in this regression analysis is the blood glucose level after eating. The explanatory variables in this regression analysis are the subject's age inputted in step S101 or step S102 and the rising indexes S1, the values of the AI, and the pulse rates PR of the pulse waves before eating and after eating that were analyzed in step S104. If the estimation expression creation device performs FFT analysis in step S104, then the explanatory variables may, for example, be the Fourier coefficients that have been calculated as the result of this FFT analysis.

On the basis of the result of the regression analysis, the estimation expression creation device creates an estimation expression for estimating the after-eating blood glucose level (step S106). An example of such an estimation expression for estimation the blood glucose level after eating is illustrated by the following Equation (1):

$$Gla = -291.2 + 1.87 \times age + 0.75 \times BLG + 1.14 \times PRb - 0.05 \times PRa + 7.17 \times Alb - 2.59 \times Ala - 0.87 \times Slb - 0.28 \times Sla \quad \text{Equation (1)}$$

In Equation (1), GLa is the blood glucose after eating, age is the age of the subject, PRb is the pulse rate PR before eating, Alb is the AI before eating, Slb is the rising index S1 before eating, PRa is the pulse rate PR after eating, Ala is the AI after eating, Sla is the rising index S1 after eating, and BLG is the blood glucose level that the subject has inputted (which is measured by blood sampling). The blood glucose level BLG that the subject inputs is the blood glucose level measured at a timing that is different from that of the estimated blood glucose level GLa. In this embodiment, the blood glucose level BLG inputted by the subject is the blood glucose level before eating as measured by blood sampling. The accuracy for estimating blood glucose level is improved by using the blood glucose level BLG as measured by blood sampling in the estimation expression.

Figure 10:
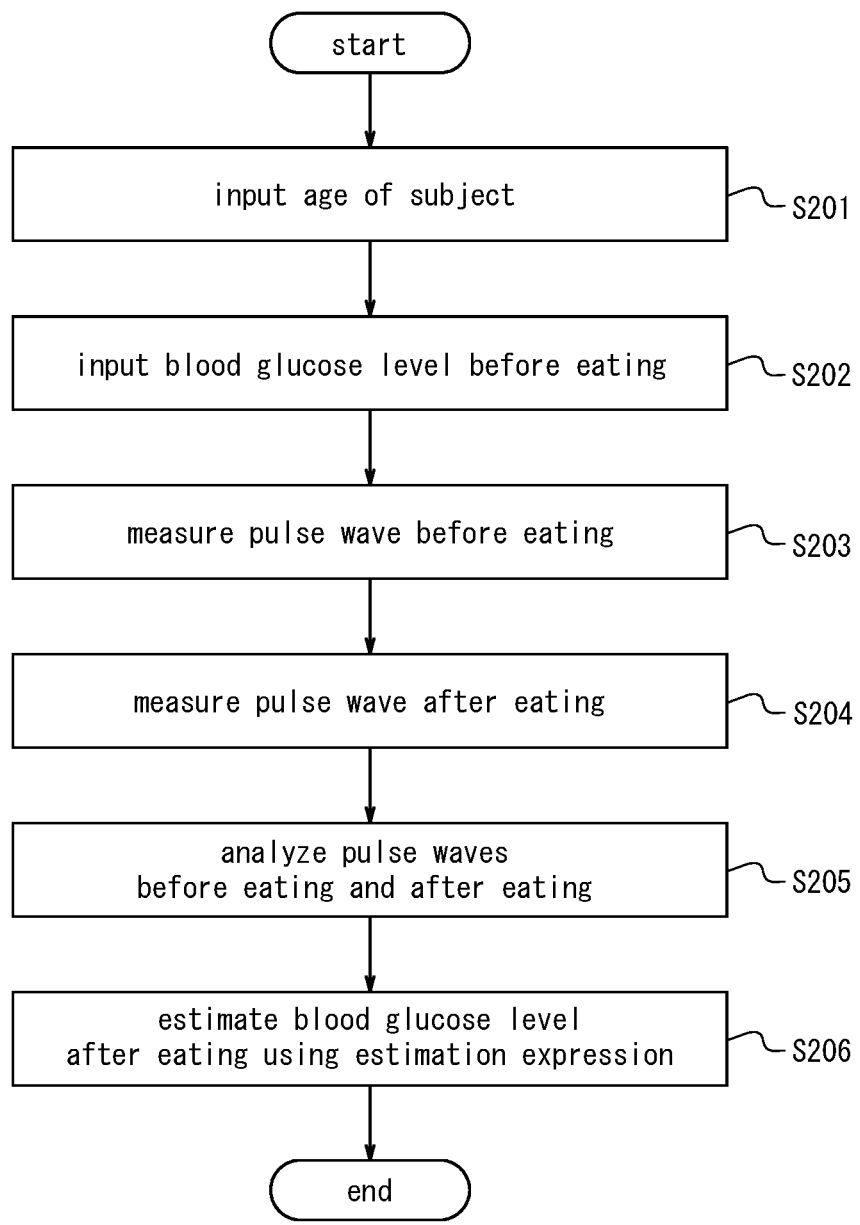
FIG. 10 is a flow chart illustrating estimation of the blood glucose level of a subject after eating performed by employing an estimation expression created by the flow of FIG. 9.

Next, a flow for estimating the blood glucose level of a subject by employing an estimation expression will be explained. FIG. 10 is a flow chart illustrating estimation of the blood glucose level of a subject after eating by employing an estimation expression that has been created according to the flow of FIG. 9. Here, the case in which the subject inputs the blood glucose level before eating measured using a blood glucose meter via the input interface 141 of the electronic device 100 will be explained.

The electronic device 100 inputs the age of the subject on the basis of operation of the input interface 141 by the subject (step S201).

On the basis of operation of the input interface 141 by the subject, the electronic device 100 then inputs the blood glucose level before eating that the subject has measured using the blood glucose meter (step S202).

On the basis of operation by the subject, the electronic device 100 measures the pulse wave of the subject before eating (step S203).

On the basis of operation by the subject after the subject has eaten, the electronic device 100 measures the pulse wave of the subject after eating (step S204).

Next, the electronic device 100 analyzes the pulse waves that have been measured (step S205). In concrete terms, the electronic device 100 may, for example, perform analysis of the rising indexes S1, of the AI, and of the pulse rates PR related to the pulse waves that have been measured.

The electronic device 100 estimates the blood glucose level after eating of the subject by applying the blood glucose level before eating inputted in step S202, the rising indexes S1, the AI, the pulse rates PR analyzed in step S205, and the age of the subject, to Equation (1) described above (step S206), for example. The blood glucose level after eating that has been estimated is notified to the subject, for example from the notification interface 147 of the electronic device 100.

Figure 11:
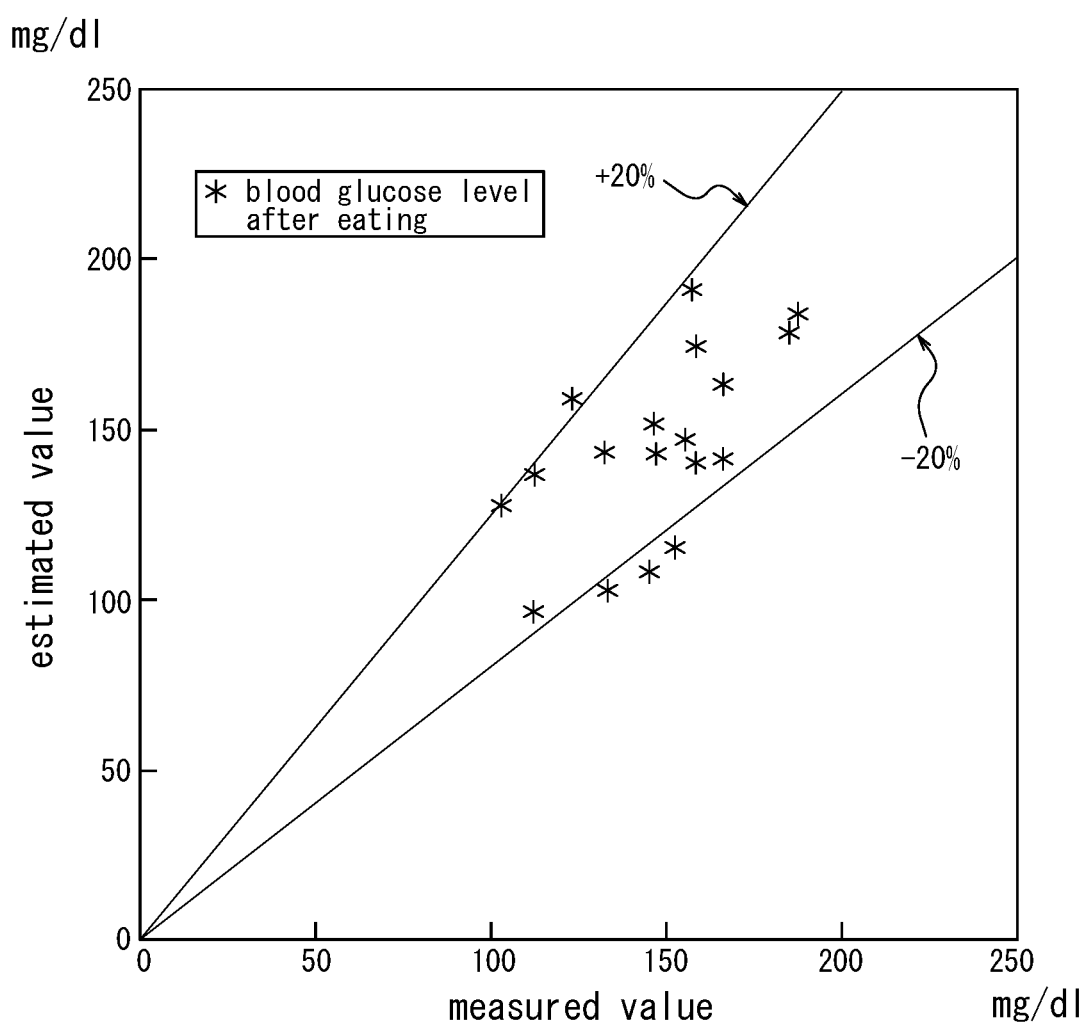
FIG. 11 is a diagram illustrating a comparison between blood glucose levels after eating estimated by employing an estimation expression created according to the flow of FIG. 9 and actually measured blood glucose levels after eating.

FIG. 11 is a diagram illustrating a comparison between blood glucose levels after eating that were estimated by employing an estimation expression created according to the flow of FIG. 9 and the actually measured blood glucose levels after eating. In the graph illustrated in FIG. 11, the measured values of blood glucose level after eating (i.e. actually measured values) are shown along the horizontal axis, and the estimated values of blood glucose level after eating are shown along the vertical axis. The measured values of blood glucose level were measured by employing a "Medisafe Fit" blood glucose meter manufactured by Terumo Co. Ltd. As is clear from FIG. 11, the measured values and the estimated values are generally included within a range of ±20%. In other words, the estimation accuracy of the estimation expression may be said to be within 20%.

In this manner, on the basis of the blood glucose level before eating which the subject measures by blood sampling, the electronic device 100 is able to estimate the blood glucose level after eating in a non-invasive manner and within a short time period. While, in this embodiment, the estimation expression was created by employing the blood glucose levels and the pulse waves before eating and after eating, the creation of the estimation expression should not be considered as being limited by this mode; it would also be possible to arrange to create the estimation expression by employing the blood glucose levels and the pulse waves either before eating or after eating. The electronic device 100 is not limited to estimating the blood glucose level after eating; it would also be possible to arrange to estimate the blood glucose level of the subject at any desired timing. This estimation of the blood glucose level at any desired timing by the electronic device can be performed in a non-invasive manner and in a short time period.

It would also be acceptable to arrange for the electronic device 100 according to the present embodiment to update the estimation expression stored in the memory 145 on the basis of the blood glucose level before eating of the subject and his pulse wave that are acquired in step S202 and step S203 during estimation of the blood glucose level. In other words, the electronic device 100 is able to use the blood glucose level before eating and the pulse wave that are acquired during estimation of the blood glucose level as sample data for updating the estimation expression. By doing this, the estimation expression is updated each time the subject performs estimation of his blood glucose level, so that the accuracy of estimation of the blood glucose level after eating by using the estimation expression is enhanced.

Embodiment 2

In the first embodiment, a case was explained in which the estimation expression was created on the basis of the blood glucose levels and the pulse waves of the subject before eating and after eating. However, in a second embodiment, an example will be explained of a case in which the estimation expression is created on the basis of the blood glucose levels and the pulse waves of the subject himself before eating and after eating.

Figure 12:
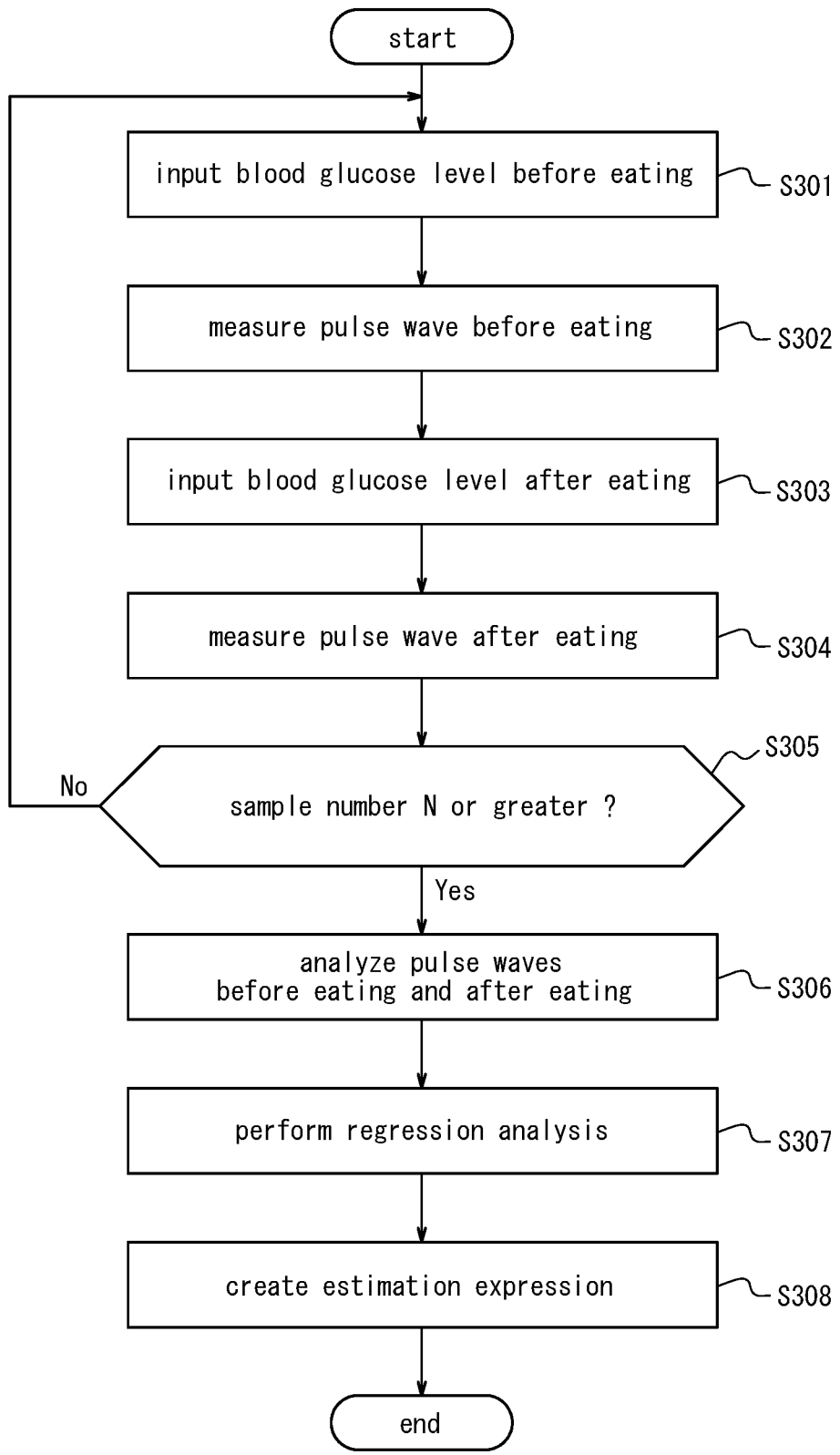
FIG. 12 is a flow chart illustrating creation of an estimation expression used by an electronic device according to a second embodiment.

FIG. 12 is a flow chart illustrating creation of an estimation expression employed by an electronic device 100 according to this second embodiment. In this embodiment, the explanation assumes that the estimation expression is created by the electronic device 100. As explained in the first embodiment, the estimation expression may also be created by an estimation expression creation device that is a different device from the electronic device 100.

Based on operation of the input interface 141 by the subject, the electronic device 100 inputs the blood glucose level before eating that the subject has measured using the blood glucose meter (step S301).

Based on operation by the subject, the electronic device 100 measures the pulse wave of the subject before eating (step S302).

After the subject has eaten, based on operation by the subject upon the input interface 141, the electronic device 100 inputs the blood glucose level after eating that the subject has measured by using the blood glucose meter (step S303). The blood glucose levels inputted in step S301 and step S303 are measured with the blood glucose meter, for example by the subject performing blood sampling.

Based on operation by the subject, the electronic device 100 measures the pulse wave of the subject after eating (step S304).

The electronic device 100 determines whether or not the number of data samples inputted in step S301 through step S304 is equal to or greater than a number N that is sufficiently great for regression analysis (step S305). This number of samples N may be determined as appropriate; for example, it may be set to 5. If the estimation expression creation device determines that the number of samples is less than N (the No case), then the estimation expression creation device repeats step S301 through step S304 until the number of samples becomes N or greater. On the other hand, if the estimation expression creation device determines that the number of samples is N or greater (the Yes case), then the flow of control proceeds to step S306 and the estimation expression is calculated.

Since the method of calculating the estimation expression in step S306 through step S308 is the same as that of step S104 through step S106 of FIG. 9, accordingly detailed explanation thereof will here be omitted. The estimation expression created by the electronic device 100 according to the flow shown in FIG. 12 is, for example, Equation (1) but with each of the coefficients altered.

Figure 13:
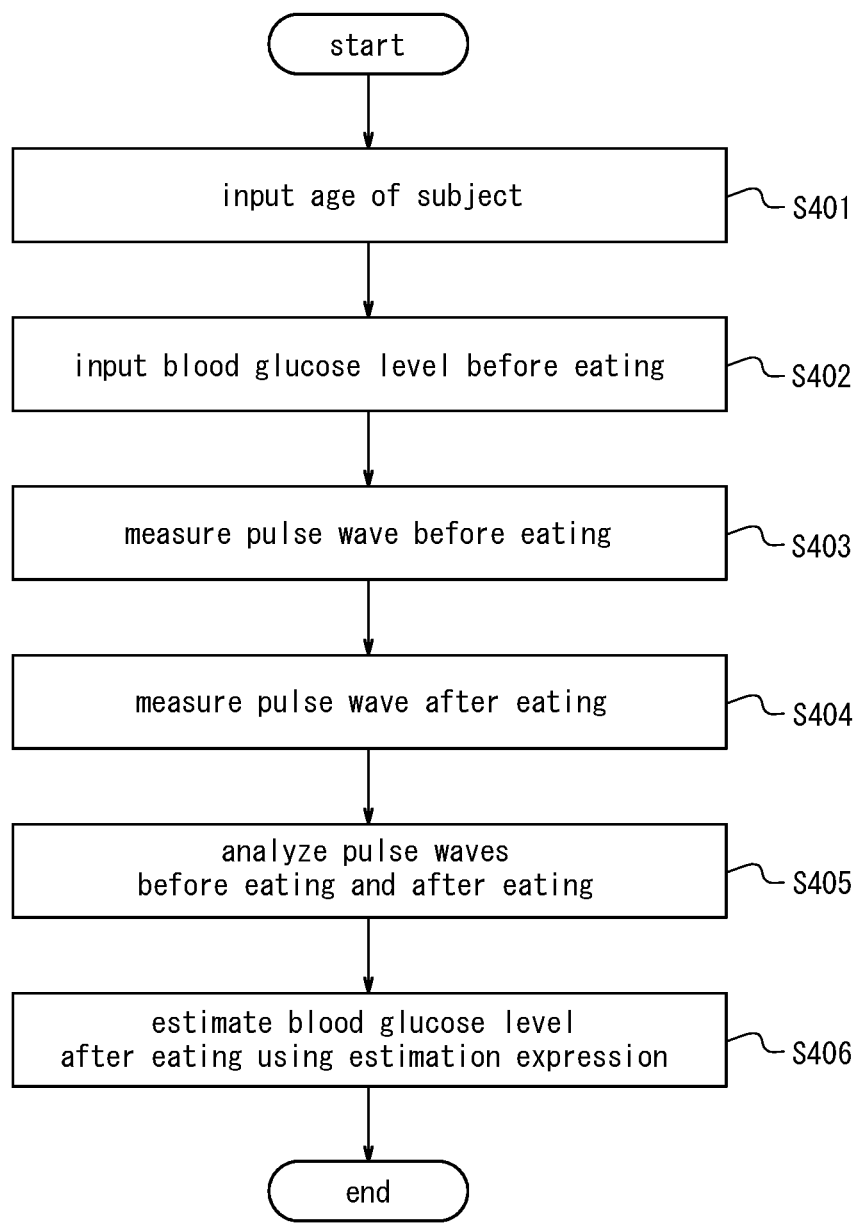
FIG. 13 is a flow chart illustrating estimation of the blood glucose level of a subject after eating performed by employing an estimation expression created by the flow of FIG. 12.

Next, a flow for estimation of the blood glucose level of the subject by employing this estimation expression will be explained. FIG. 13 is a flow chart illustrating estimation of the blood glucose level of a subject after eating performed by employing an estimation expression created by the flow of FIG. 12. Here, a case in which the subject inputs a blood glucose level measured by using a blood glucose meter via the input interface 141 of the electronic device 100 will be explained.

The electronic device 100 inputs the age of the subject based on operation of the input interface 141 by the subject (step S401).

Based on operation of the input interface 141 by the subject, the electronic device 100 inputs the blood glucose level before eating that the subject has measured using the blood glucose meter (step S402).

Based on operation by the subject, the electronic device 100 measures the pulse wave of the subject before eating (step S403).

Based on operation by the subject after eating, the electronic device 100 measures the pulse wave of the subject after eating (step S404).

The electronic device 100 analyzes the pulse waves that have been measured (step S405). In concrete terms, the electronic device 100 may, for example, perform analysis of the rising indexes S1, the AI, and the pulse rates PR related to the pulse waves that have been measured.

The electronic device 100 estimates the blood glucose level after eating of the subject by applying the rising indexes S1, the AI, and the pulse rates PR analyzed in step S405 and the age of the subject to, for example, the estimation expression created by the flow chart of FIG. 12 (step S406). The blood glucose level after eating that has been estimated is notified to the subject, for example from the notification interface 147 of the electronic device 100.

In this manner, on the basis of the blood glucose level before eating which the subject measures by blood sampling, the electronic device 100 is able to estimate the blood glucose level after eating in a non-invasive manner and within a short time period. Since, in this embodiment, the estimation expression for estimating the blood glucose level after eating is created on the basis of sample data acquired from the subject, accordingly the accuracy of estimation of the glucose level of that subject after eating is enhanced.

In a similar manner to the explanation of the first embodiment, it would also be acceptable to arrange for the electronic device 100 according to this embodiment, for estimation of the blood glucose level, to update the estimation expression stored in the memory 145 on the basis of the blood glucose level before eating and the pulse wave of the subject acquired in step S402 and step S403. By doing this, the estimation expression is updated every time the subject performs estimation of his blood glucose level, so that the accuracy of estimation of his blood glucose level after eating using the estimation expression is enhanced.

It would also be acceptable, when it is possible to gather a sufficient number of samples of sample data from the subject, to arrange for the electronic device 100 to estimate the blood glucose level, not by employing the blood glucose level that has been measured by blood sampling, but rather on the basis of the pulse wave of the subject. For example, the electronic device 100 may estimate the blood glucose level of the subject before eating on the basis of the pulse wave of the subject before eating. By doing this, and by the subject measuring his pulse wave before eating by employing the electronic device 100, it is possible for the electronic device 100 to estimate the blood glucose level of the subject before eating by employing an estimation expression that is based upon the pulse wave before eating. In this case, the electronic device is able to estimate the blood glucose level before eating as well in a non-invasive manner and moreover in a short period of time. A sufficient amount of sample data means an amount of data such that an estimation expression can be created that is capable of estimating the blood glucose level before eating of the subject on the basis of his pulse wave before eating at an accuracy that is at least a predetermined accuracy. The blood glucose level that is estimated is not limited to being the one before eating; it would also be acceptable to arrange to estimate the blood glucose level after eating on the basis of the pulse wave after eating. Moreover, the blood glucose level that is estimated is not limited to being the one before eating or the one after eating; it would also be possible to arrange to estimate the blood glucose level at any desired timing on the basis of the pulse wave that is measured at any suitable timing.

Embodiment 3

In the first embodiment, a case was explained in which the electronic device 100 estimates the blood glucose level of the subject after eating. However, in this third embodiment, a case will be explained in which the electronic device 100 estimates a lipid value of the subject after eating. Here, the term "lipid value" encompasses neutral fat, total cholesterol, HDL cholesterol, LDL cholesterol, and so on. In the explanation of this third embodiment, explanation of features that are the same as features of the first embodiment will be omitted as appropriate.

With an electronic device 100, for example, an estimation expression for estimating the lipid value on the basis of the pulse waves may be stored in advance in the memory 145. The electronic device 100 estimates the lipid value by using this estimation expression.

The estimation theory related to estimation of the lipid value on the basis of the pulse waves is the same as the theory of estimation of blood glucose level that was explained for the first embodiment. In other words, changes in the levels of the lipid in the blood of the subject are also reflected in changes in the waveform of the pulse waves. Due to this, the electronic device 100 is able to acquire the pulse waves, and to estimate the lipid value on the basis of changes in the pulse waves that have thus been acquired. It is possible further to enhance the accuracy of estimation of the lipid value by inputting the blood glucose levels during lipid estimation to the electronic device 100, together with the pulse waves.

Figure 14:
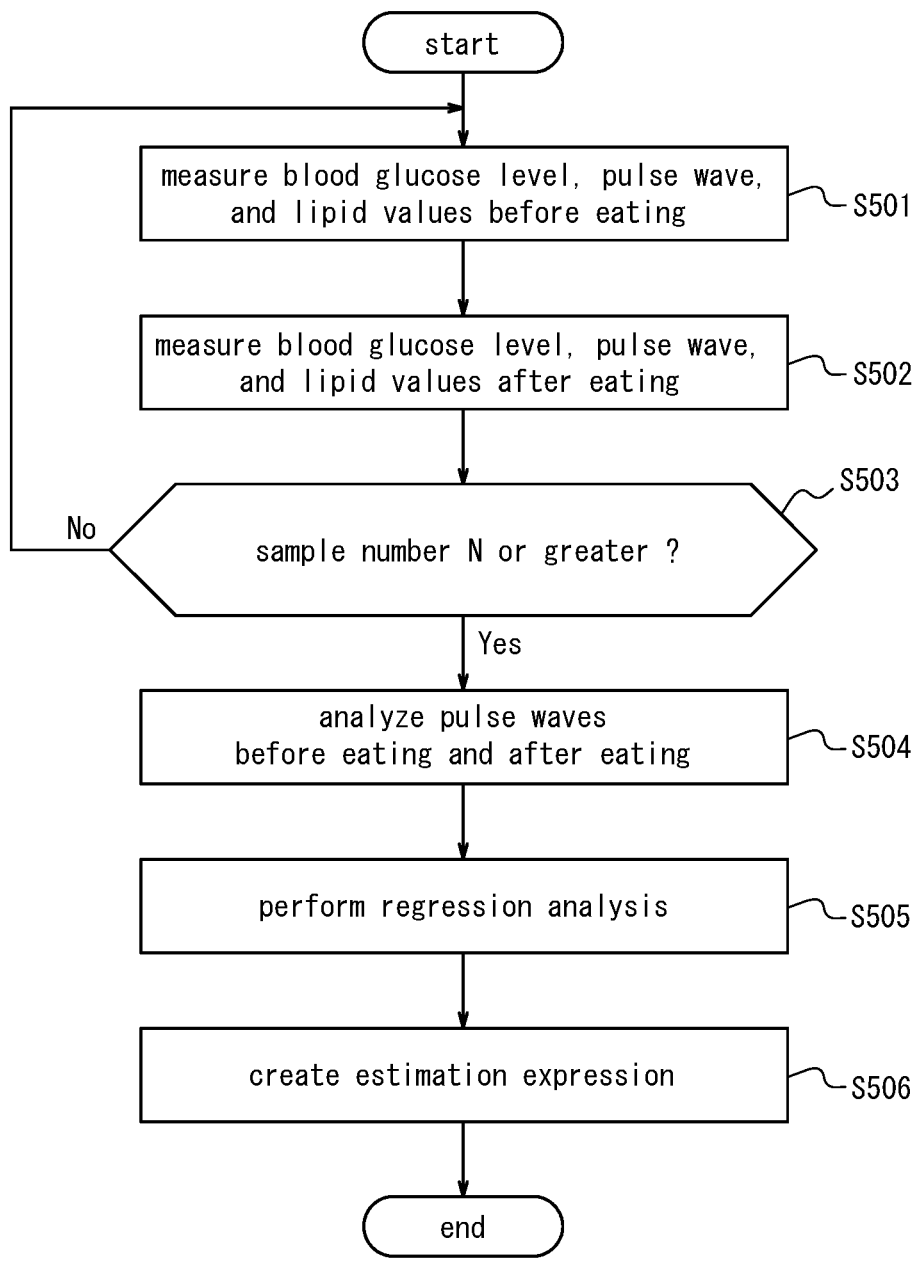
FIG. 14 is a flow chart illustrating creation of an estimation expression used by an electronic device according to a third embodiment

FIG. 14 is a flow chart illustrating a flow for creation of an estimation expression used by the electronic device 100 according to this embodiment. In this embodiment, the estimation expression is created by performing regression analysis on the basis of sample data. Moreover, in this embodiment, the estimation expression is created on the basis of the pulse wave, the lipid value, and the blood glucose level before eating, which serve as the sample data. In this embodiment, "before eating" means when the stomach of the subject is empty. And "after eating" means after a predetermined time period has elapsed for the lipid value to rise after eating (for example, about three hours after the subject has started eating). In creating the estimation expression, in particular, by creating the estimation expression by performing regression analysis using sample data for which the variation of the lipid value is close to a normal distribution, it is possible to estimate the lipid value of the subject who is to be the examinee at any desired timing, irrespective of whether that timing is before eating or after eating.

In creating the estimation expression, first, information is inputted to the estimation expression creation device related to the blood glucose level, the pulse wave associated with the blood glucose level, and the lipid value before eating, as measured by the blood glucose meter, a pulse wave meter, and a lipid measurement device respectively (step S501).

Information is inputted to the estimation expression creation device related to the blood glucose level, the pulse wave associated with the blood glucose level, and the lipid value after eating, as measured by the blood glucose meter, the pulse wave meter, and the lipid measurement device respectively (step S502). The blood glucose levels inputted in step S501 and step S502 may, for example, be measured with a blood glucose meter by performing blood sampling.

In step S501 or step S502, the age of the subject of each set of sample data is also inputted.

The estimation expression creation device then determines whether the number of samples in the sample data inputted in step S501 and step S502 is at least a number N that is sufficient for performing regression analysis (step S503). This number of samples N may be determined in any appropriate manner; for example, it may be set to 100. If the estimation expression creation device determines that the number of samples is less than N (the No case), then step S501 and step S502 are repeated until the number of samples becomes N or greater. On the other hand, if the estimation expression creation device determines that the number of samples is at least N (the Yes case), then the flow of control proceeds to step S504, and calculation of the estimation expression is performed.

In this calculation of the estimation expression, the estimation expression creation device analyzes the pulse waves before eating and after eating (step S504). In this embodiment, the estimation expression creation device performs analysis of the rising indexes S1, of the AI, and of the pulse rates PR before eating and after eating. The estimation expression creation device may perform FFT analysis as analysis of the pulse waves.

The estimation expression creation device then performs regression analysis (step S505). The objective variable in this regression analysis is the lipid values after eating. And the explanatory variables in this regression analysis are the subject's age inputted in step S501 or step S502 and the rising indexes S1, the values of the AI, and the pulse rates PR of the pulse waves before eating and after eating that were analyzed in step S504. If the estimation expression creation device performs FFT analysis in step S504, then the explanatory variables may, for example, be the Fourier coefficients that are calculated as results of this FFT analysis.

On the basis of the results of the regression analysis, the estimation expression creation device creates an estimation expression for estimating the after-eating lipid value (step S506).

Figure 15:
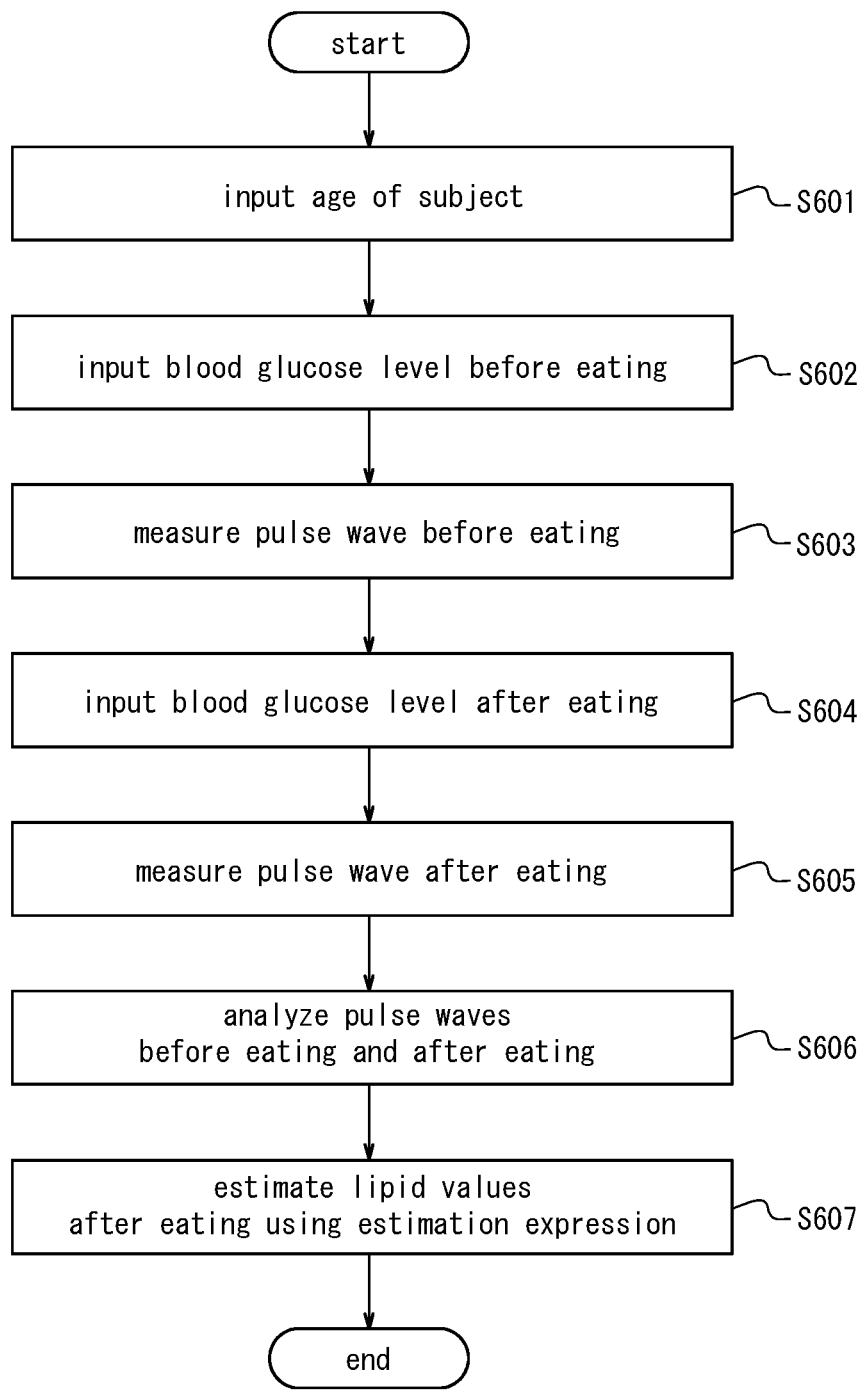
FIG. 15 is a flow chart illustrating estimation of a lipid value of a subject after eating performed by employing an estimation expression created by the flow of FIG. 14.

Next, a flow for estimating the lipid value of a subject by employing an estimation expression will be explained. FIG. 15 is a flow chart illustrating estimation of the lipid value of a subject after eating by employing an estimation expression created by the flow of FIG. 14. Here, the case in which the subject inputs the blood glucose level before eating measured using a blood glucose meter via the input interface 141 of the electronic device 100 will be explained.

The electronic device 100 inputs the age of the subject on the basis of operation of the input interface 141 by the subject (step S601).

Based on operation of the input interface 141 by the subject, the electronic device 100 then inputs the blood glucose level before eating that the subject has measured using a blood glucose meter (step S602).

Based on operation by the subject, the electronic device 100 measures the pulse wave of the subject before eating (step S603).

After the subject has eaten, based on operation by the subject, the electronic device 100 inputs the blood glucose level after eating that the subject has measured using the blood glucose meter (step S604).

Based on operation by the subject, the electronic device 100 measures the pulse wave of the subject after eating (step S605).

The electronic device 100 analyzes the pulse waves that have been measured (step S606). In concrete terms, the electronic device 100 may, for example, perform analysis of the rising indexes S1, of the AI, and of the pulse rates PR related to the pulse waves that have been measured.

The electronic device 100 estimates the lipid value of the subject after eating by applying the rising indexes S1, the AI, and the pulse rates PR analyzed in step S606 and the age of the subject to, the estimation expression that was created by the flow chart of FIG. 14 (step S607). The lipid value after eating that has thus been estimated is notified to the subject, for example from the notification interface 147 of the electronic device 100.

Figure 16:
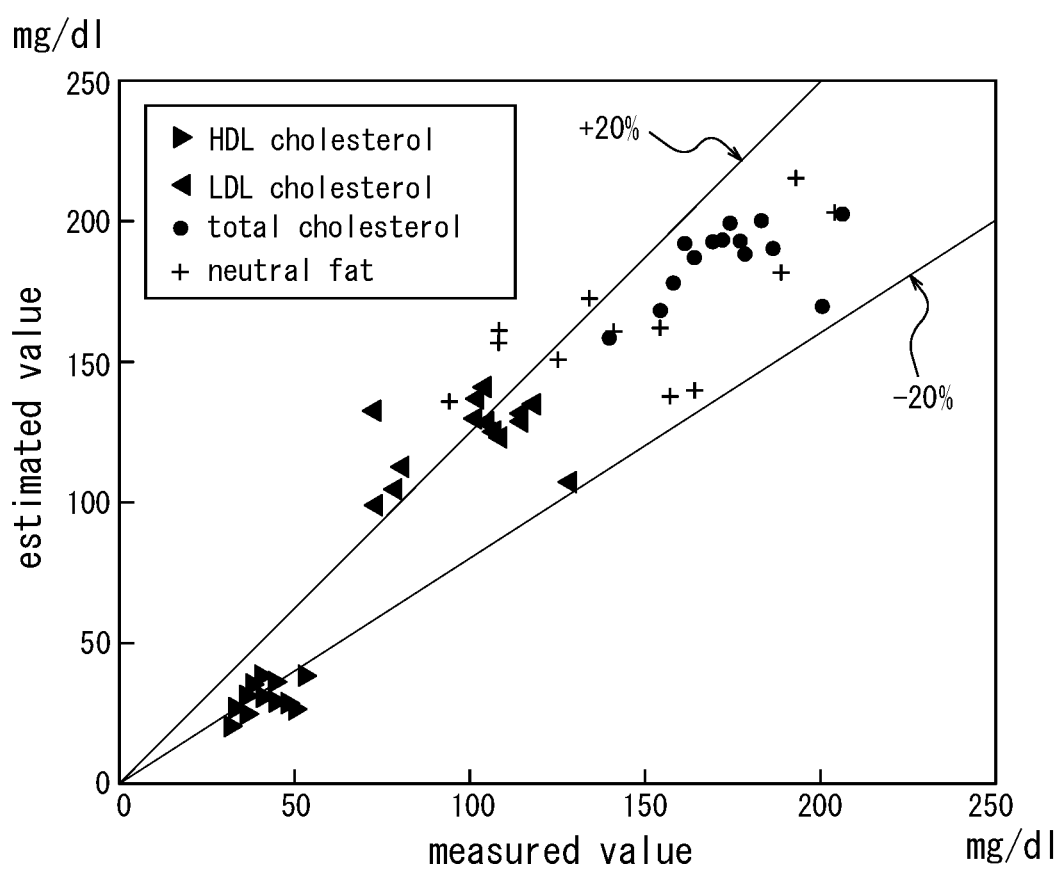
FIG. 16 is a diagram illustrating a comparison between lipid level after eating estimated by employing an estimation expression created according to the flow of FIG. 14 and actually measured lipid level after eating.

FIG. 16 is a diagram illustrating a comparison between lipid levels after eating estimated by employing an estimation expression created according to the flow of FIG. 14 and actually measured lipid levels after eating. In the graph illustrated in FIG. 16, the measured values of the lipid values after eating (i.e. actually measured values) are shown along the horizontal axis, and the estimated values of the lipid values after eating are shown along the vertical axis. The measured values of the lipid values were measured by employing a "cobas b 101" made by Roche Diagnostics Ltd. As is clear from FIG. 16, the measured values and the estimated values are generally included within a range of ±20%. In other words, the estimation accuracy of the estimation expression may be said to be within 20%.

In this manner, the electronic device 100 is able to estimate the lipid value after eating on the basis of the blood glucose levels before eating and after eating which the subject measures by blood sampling.

The electronic device 100 estimates the lipid value by using the blood glucose levels before eating and after eating. Due to this, the electronic device 100 is able to estimate the lipid value by correcting for (i.e. by eliminating) influence exerted by the blood glucose level upon the pulse wave after eating. Therefore, according to this electronic device 100, the accuracy of estimation of the lipid values is enhanced.

While, in this embodiment, the estimation expression was created by employing the blood glucose levels, the pulse waves, and the lipid values before eating and after eating, the creation of the estimation expression should not be considered as being limited by this mode; it would also be possible to arrange to create the estimation expression by employing the blood glucose levels, the pulse waves, and the lipid values either before eating or after eating. The electronic device 100 is not limited to estimating the lipid values after eating; it would also be possible to arrange to estimate the lipid values of the subject at any desired timing. This estimation of the lipid values at any desired timing by the electronic device can be performed in a non-invasive manner and in a short time period.

It would also be acceptable to arrange for the electronic device 100 according to the present embodiment to update the estimation expression, in a similar manner to that explained in connection with the first embodiment. In other words, it would be acceptable to arrange for the electronic device 100 to update the estimation expression stored in the memory 145 for estimation of the lipid values, on the basis of the blood glucose level and the pulse wave of the subject before eating and his blood glucose level and pulse wave after eating that were acquired in step S602 through step S605. By doing this, the estimation expression is updated each time the subject performs estimation of his blood glucose level, so that the accuracy of estimation of the lipid values after eating by using the estimation expression is enhanced.

In the first and second embodiments described above, examples have been explained of cases in which, when estimating the blood glucose level after eating by employing the electronic device 100, the subject inputs the blood glucose level before eating that he has measured using a blood glucose meter by employing the input interface 141 of the electronic device 100. However, it would also be acceptable to arrange for the blood glucose level before eating to be inputted automatically, for example from a blood glucose meter to the electronic device 100.

Figure 17:
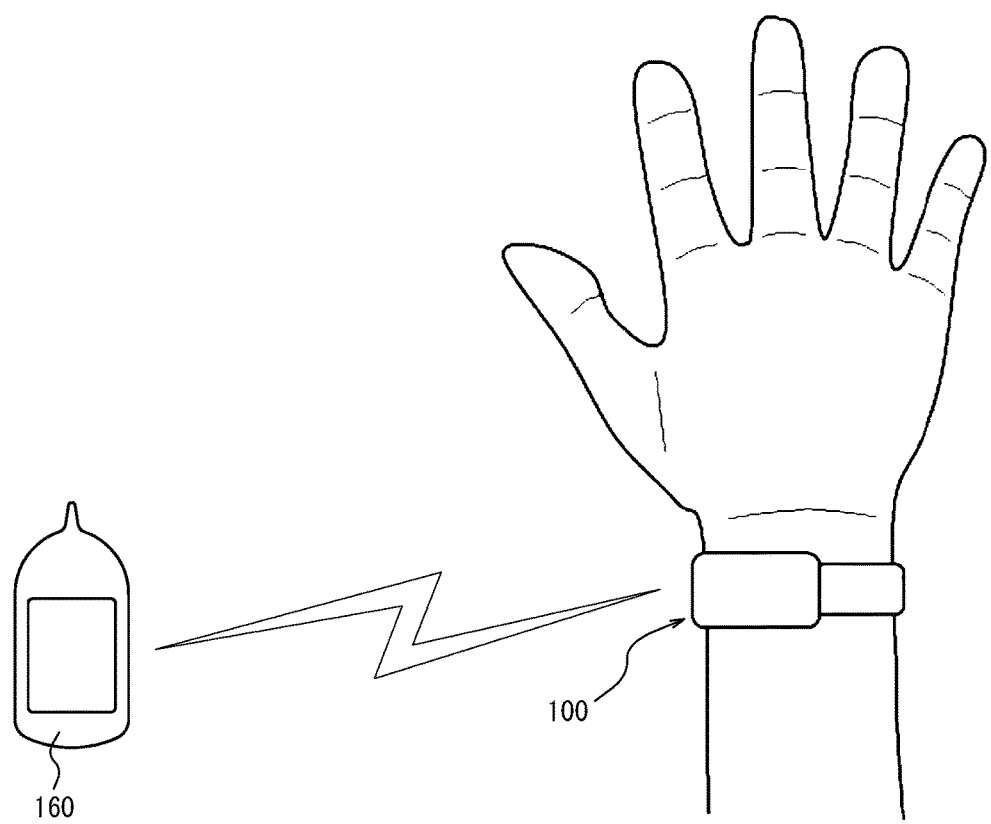
FIG. 17 is a diagram schematically illustrating communication between an electronic device and a blood glucose meter.

FIG. 17 is a diagram schematically illustrating communication between an electronic device 100 and a blood glucose meter 160. The blood glucose meter 160 includes a communication interface, and is capable of transmitting and receiving information via the communication interface 146 of the electronic device 100. When measuring the blood glucose level of a subject (i.e. the blood glucose level before eating) on the basis of operation by the subject, the blood glucose meter 160, for example, may transmit the blood glucose level that is the result of measurement to the electronic device 100. Using the blood glucose level that has thus been acquired from the blood glucose meter 160, the electronic device 100 may, for example, estimate the blood glucose level after eating of the subject according to the flow described in FIG. 10 or FIG. 13 and so on.

In a similar manner to the case with the third embodiment, it may be arranged for the electronic device 100 to acquire the blood glucose level from the blood glucose meter 160 with which it is capable of communicating. In this case, the electronic device 100 can estimate a lipid value on the basis of the blood glucose level acquired from the blood glucose meter 160.

In the embodiment described above, an example has been explained of a case in which the estimation of the blood glucose level and the lipid value is performed by the electronic device 100, but it would also be acceptable for this estimation of the blood glucose level and the lipid value not necessarily to be performed by the electronic device 100. An example will now be explained of a case in which the estimation of the blood glucose level and the lipid value is performed by a device other than the electronic device 100.

Figure 18:
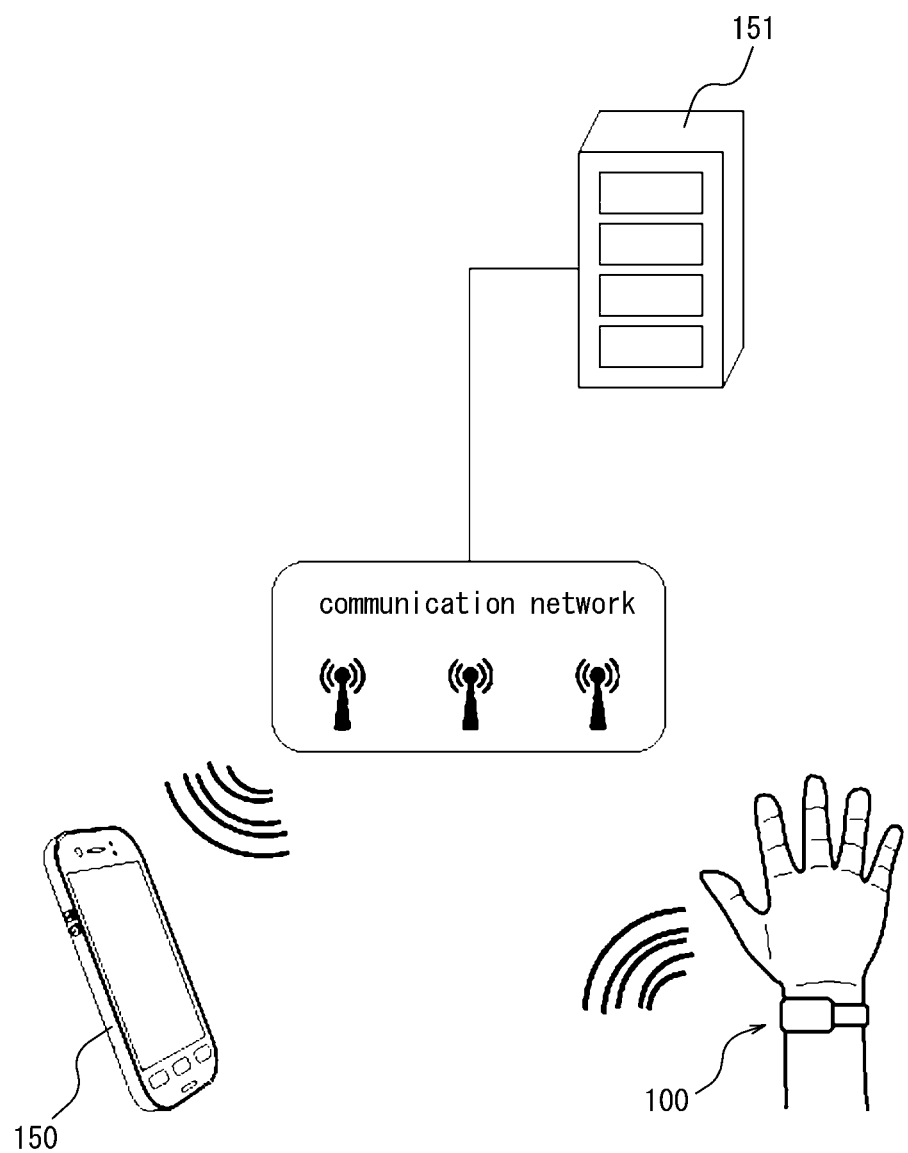
FIG. 18 is a schematic diagram illustrating the general structure of a system according to an embodiment.

FIG. 18 is a schematic diagram illustrating the general structure of a system according to an embodiment. The system illustrated in FIG. 18 comprises a server 151, a portable terminal 150, and a communication network. As illustrated in FIG. 18, the pulse wave measured by the electronic device 100 is transmitted to the server 151 via the communication network, and is stored upon the server 151 as information individual to this subject personally. The blood glucose level of the subject or his lipid values are estimated by the server 151 by comparison with information for this subject acquired in the past, and/or with databases of various types. It would also be acceptable to arrange for the server 151 further to generate optimum advice for the subject. The server 151 returns the result of estimation and the advice to the portable terminal 150 which the subject owns. And this system can be set up so that the portable terminal 150 notifies the estimation result and the advice that it has thus received to a display unit of the portable terminal 150. It is possible further to enhance the accuracy of estimation by employing the communication function of the electronic device 100 in this way, since it is possible for information from a plurality of users to be gathered by the server 151. And, since the portable terminal 150 is employed as a notification means, accordingly the notification interface 147 of the electronic device 100 becomes unnecessary, which means that the electronic device can be made more compact. Furthermore since, with this electronic device 100, the server 151 estimates the blood glucose level or the lipid level of the subject, accordingly it is possible to reduce the burden of calculation upon the controller 143 of the electronic device 100. With this electronic device 100, since the information acquired from the subject in the past is stored upon the server 151, it is possible to reduce the burden upon the memory 145 of the electronic device 100. It therefore becomes possible to make the electronic device 100 yet more compact, and to simplify its construction yet further. The calculation processing speed is also enhanced.

For the system according to this embodiment, a structure has been illustrated in which the electronic device 100 and the portable terminal 150 are connected together via the server 151 by a communication network. However, the system according to this disclosure is not to be considered as being limited to this structure. It would also be acceptable not to employ any server 151, but rather to connect the electronic device 100 and the portable terminal 150 together directly via a direct communication network.

A plurality of concrete examples have been described in order fully and clearly to describe the present disclosure. However, it should be understood that the appended Claims are not to be considered as being limited by the embodiments described above; all variant embodiments and alternative configurations that can be implemented by a person skilled in this technical field should be considered as coming within the scope of the basic subject matter described in this specification.

For example, in the embodiments described above, cases have been explained in which an angular velocity sensor has been provided as the sensor 130. However, the electronic device 100 according to this disclosure is not to be considered as being limited to this possibility. The sensor 130 may include an optical pulse wave sensor that has a light emission unit and a light reception unit, or may include a pressure sensor. Moreover, the site at which the electronic device 100 is worn is not limited to being upon the wrist of the subject. The sensor 130 may be disposed over an artery on the neck of the subject, or over an artery on his ankle, his thigh, his ear, or the like.

The invention claimed is:

1. An electronic device, comprising:
a sensor configured to acquire a pulse wave of a subject; and
a controller configured to estimate a blood glucose level of the subject on the basis of an estimation expression created on the basis of a blood glucose level, a pulse wave corresponding to the blood glucose level, and the pulse wave of the subject acquired by the sensor, by performing regression analysis on a rising index based upon a slope of the pulse wave of the subject acquired by the sensor, an augmentation index given by a ratio of magnitudes of forward and reflected waves of the pulse wave of the subject, and a pulse rate of the subject.

2. An electronic device according to claim 1, wherein the estimation expression is created on the basis of the blood glucose level of the subject and the pulse wave corresponding to the blood glucose level.

3. An electronic device according to claim 1, wherein the controller is further configured to estimate the blood glucose level of the subject after eating on the basis of the blood glucose level of the subject before eating.

4. An electronic device according to claim 1, wherein the controller is configured to update the estimation expression on the basis of the blood glucose level and the pulse wave of the subject before eating.

5. An electronic device, comprising:
a sensor configured to acquire a pulse wave of a subject; and
a controller configured to estimate a lipid value of the subject on the basis of an estimation expression created on the basis of a blood glucose level and a pulse wave corresponding to the blood glucose level, and the pulse wave of the subject acquired by the sensor, by performing regression analysis on a rising index based upon a slope of the pulse wave of the subject acquired by the sensor, an augmentation index given by a ratio of magnitudes of forward and reflected waves of the pulse wave of the subject, and a pulse rate of the subject.

6. An estimation system, comprising:
a blood glucose meter configured to measure a blood glucose level of a subject; and
an electronic device having a sensor configured to acquire a pulse wave of the subject;
wherein the electronic device is configured to estimate the blood glucose level of the subject on the basis of an estimation expression created on the basis of a blood glucose level, a pulse wave corresponding to the blood glucose level, the blood glucose level of the subject measured by the blood glucose meter, and the pulse wave of the subject acquired by the sensor, by performing regression analysis on a rising index based upon a slope of the pulse wave of the subject acquired by the sensor, an augmentation index given by a ratio of magnitudes of forward and reflected waves of the pulse wave of the subject, and a pulse rate of the subject.

7. An estimation system, comprising:
a blood glucose meter configured to measure a blood glucose level of a subject; and
an electronic device having a sensor configured to acquire a pulse wave of the subject;
wherein the electronic device is configured to estimate a lipid value of the subject on the basis of an estimation expression created on the basis of blood glucose level, a pulse wave corresponding to the blood glucose level, the blood glucose level of the subject measured by the blood glucose meter, and the pulse wave of the subject acquired by the sensor, by performing regression analysis on a rising index based upon a slope of the pulse wave of the subject acquired by the sensor, an augmentation index given by a ratio of magnitudes of forward and reflected waves of the pulse wave of the subject, and a pulse rate of the subject.

8. An electronic device according to claim 1, wherein the sensor is a motion sensor.

9. An electronic device according to claim 8, wherein the motion sensor comprises at least one of an angular velocity sensor, an acceleration sensor, and an angle sensor.

10. An electronic device according to claim 1, wherein the sensor is configured to acquire the pulse wave of the subject through displacement of the sensor.

11. An electronic device according to claim 10, further comprising:
an elastic member in contact with the sensor,
wherein the sensor is configured to acquire the pulse wave of the subject through displacement of the sensor on the elastic member.

12. An electronic device according to claim 1, further comprising:
a front surface; and
a rear surface opposing the front surface,
wherein the sensor protrudes from the rear surface.

* * * * *